(12) United States Patent
Baumgaertel et al.

(10) Patent No.: US 10,067,095 B2
(45) Date of Patent: Sep. 4, 2018

(54) METHOD AND DEVICE FOR DETECTING A STRUCTURE-BORNE SOUND SIGNAL, IN PARTICULAR FOR DETECTING A STRUCTURE-BORNE SOUND SIGNAL TRIGGERED BY AN OCCURRENCE OF DAMAGE ON A COMPONENT TO BE MONITORED

(71) Applicant: Hella KGaA Hueck & Co., Lippstadt (DE)

(72) Inventors: Hauke Baumgaertel, Delmenhorst (DE); Thomas Niemann, Delmenhorst (DE); Bastian Kanning, Bremen (DE); Volker Skwarek, Wesenberg (DE)

(73) Assignee: Hella KGAA Hueck & Co., Lippstadt (DE)

( * ) Notice: Subject to any disclaimer, the term of this patent is extended or adjusted under 35 U.S.C. 154(b) by 207 days.

(21) Appl. No.: 14/995,884

(22) Filed: Jan. 14, 2016

(65) Prior Publication Data

US 2016/0209370 A1 Jul. 21, 2016

(30) Foreign Application Priority Data

Jan. 15, 2015 (DE) ........................ 10 2015 000 207

(51) Int. Cl.
*G01N 29/24* (2006.01)
*G01N 29/14* (2006.01)

(52) U.S. Cl.
CPC ......... *G01N 29/2437* (2013.01); *G01N 29/14* (2013.01); *G01N 29/2475* (2013.01)

(58) Field of Classification Search
CPC ............... G01N 29/2437; G01N 29/14; G01N 29/2475; G01N 29/245; G01N 29/2443; G01N 29/22; G01N 29/2223; G01N 29/24
USPC .................. 73/645, 587, 591, 646, 649, 661
See application file for complete search history.

(56) References Cited

U.S. PATENT DOCUMENTS

| 4,437,332 | A |   | 3/1984 | Pittaro |
| 5,029,474 | A | * | 7/1991 | Schulze .................. G01H 1/00 73/587 |
| 5,119,002 | A |   | 6/1992 | Kato et al. |
| 5,138,241 | A | * | 8/1992 | Shimizu ................ B60S 1/0818 318/444 |

(Continued)

FOREIGN PATENT DOCUMENTS

| DE | 3327526 | 4/1984 |
| DE | 4033332 | 4/1991 |

(Continued)

*Primary Examiner* — Manish S Shah
*Assistant Examiner* — Rose M Miller
(74) *Attorney, Agent, or Firm* — Muncy, Geissler, Olds & Lowe, P.C.

(57) ABSTRACT

A device for detecting a structure-borne sound signal, in particular for detecting a structure-borne sound signal caused by an event of damage on a component to be monitored, having at least one structure-borne sound sensor, at least one signal-conducting connection of the structure-borne sound sensor to an evaluation device, and a protective body. The structure-borne sound sensor has a structure-borne sound-conducting connection to the protective body and the protective body has a structure-borne sound-conducting connection to the component to be monitored.

13 Claims, 1 Drawing Sheet

(56) References Cited

U.S. PATENT DOCUMENTS

| | | | |
|---|---|---|---|
| 5,714,687 A * | 2/1998 | Dunegan | G01H 1/00 |
| | | | 73/587 |
| 5,847,826 A * | 12/1998 | Fukui | B60S 1/0818 |
| | | | 318/DIG. 2 |
| 5,936,163 A | 8/1999 | Greathouse | |
| 7,469,595 B2 * | 12/2008 | Kessler | G01L 1/162 |
| | | | 73/583 |
| 2004/0232773 A1 | 11/2004 | Parker et al. | |
| 2005/0061076 A1 * | 3/2005 | Kim | G01H 9/004 |
| | | | 73/587 |
| 2006/0213272 A1 * | 9/2006 | Yoshioka | F16C 29/00 |
| | | | 73/580 |
| 2007/0012111 A1 * | 1/2007 | Kim | G01H 9/004 |
| | | | 73/594 |

FOREIGN PATENT DOCUMENTS

| | | |
|---|---|---|
| DE | 10034524 | 1/2002 |
| DE | 102004018219 | 11/2005 |
| JP | S59031447 | 2/1984 |

* cited by examiner

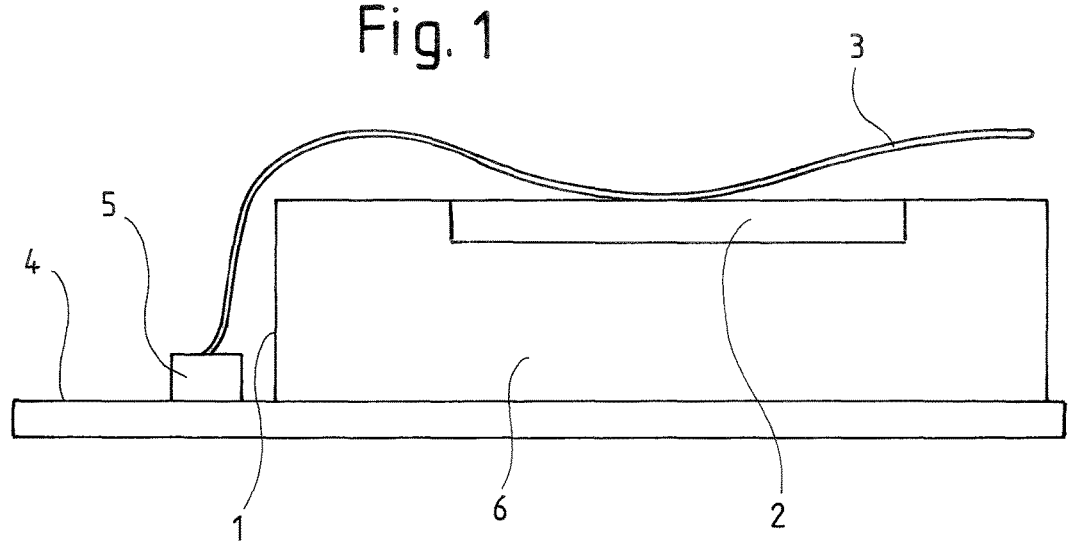
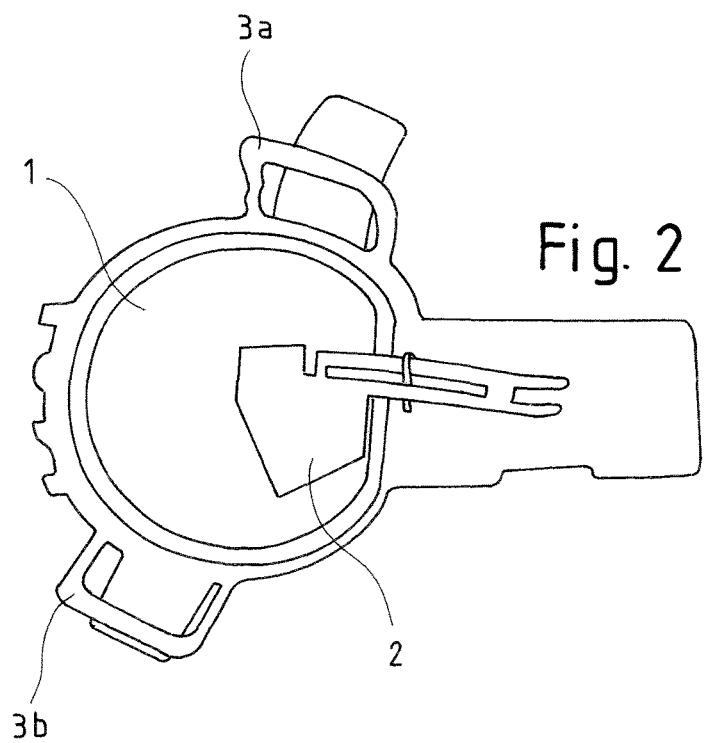

METHOD AND DEVICE FOR DETECTING A STRUCTURE-BORNE SOUND SIGNAL, IN PARTICULAR FOR DETECTING A STRUCTURE-BORNE SOUND SIGNAL TRIGGERED BY AN OCCURRENCE OF DAMAGE ON A COMPONENT TO BE MONITORED

BACKGROUND OF THE INVENTION

Field of the Invention

The invention relates to a device for detecting a structure-borne sound signal, in particular for detecting a structure-borne sound signal triggered by an occurrence of damage on a component to be monitored, having at least one structure-borne sound sensor, at least one signal-conducting connection of the structure-borne sound sensor to an evaluation device and having a protective body. Furthermore, the invention relates to a vehicle, in particular a motor vehicle having a previously-defined device.

Brief Discussion of the Related Art

Devices and methods for detecting occurrence of damage are known and are applied many times in modern motor vehicles. For example, a device for detecting a deformation due to an accident of at least one component of a motor vehicle is known from De 100 34 524 A1. Here, the device comprises a sensor device by means of which structure-borne sound frequency ranges of a component of the vehicle are detectable. For evaluation of the sensor signals, the device comprises an evaluation device. Furthermore, the device comprises at least one pulse generator, by means of which a frequency pulse for exciting at least one component of the motor vehicle can be generated. By significant changes of the structure-borne sound frequency range relative to a previously-detected structure-borne sound frequency range, a deformation that is due to an occurrence of damage of the respective component is assumed.

Mostly, sensor devices for detecting occurrence of damage or contact on a motor vehicle via the evaluation of structure-borne sound signals are directly fixed on the component to be monitored. For example, piezoelectric films are used as structure-borne sound sensors, which are bonded to the respective component. For example, structure-borne sound sensors are fixedly bonded to a motor vehicle windshield to be monitored to ensure good transmission of the structure-borne sound. These connections often are not releasable so that a non-destructive dismounting of the structure-borne sound sensor is difficult. In addition, evaluation electronics for evaluating the structure-borne sound signals need to be protected against external environmental impacts, e.g. by means of a housing. In this case, there are options of arranging the structure-borne sound sensor including the evaluation electronics in a housing, which housing is then directly bonded to the windshield to be monitored. Another option is to separately bond the structure-borne sound sensor to the windshield, wherein an electric connection to the evaluation electronics located in a housing is to be established. A shielding of the structure-borne sound sensor with the evaluation electronics in a housing connected thereto may lead to a dampened transmission of the structure-borne sound signals to the structure-borne sound sensor. Thus, a detection of structure-borne signals of low intensity can be more difficult.

SUMMARY OF THE INVENTION

The object of the invention is to propose a device for detecting a structure-borne sound signal, in which the structure-borne sound sensor is protected against external environmental impacts and which enables enhancing the structure-borne sound signals to be detected.

Said object is achieved by means of a device for detecting a structure-borne sound signal, in particular for detecting a structure-borne sound signal triggered by an occurrence of damage on a component to be monitored, having at least one structure-borne sound sensor, at least one signal-conducting connection of the structure-borne sound sensor to an evaluation device and having a protective body, characterized in that the structure-borne sound sensor comprises a structure-borne sound conducting connection to the protective body and the protective body comprises a structure-borne sound conducting connection to the component to be monitored, and a vehicle, in particular a motor vehicle, having this device. Further developments and advantageous embodiments are indicated in the claims.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 illustrates a sectional partial view of a device according to the invention on a surface to be monitored; and FIG. 2 illustrates a perspective view of a device according to the invention in a top view on the side facing the surface to be monitored.

DETAILED DESCRIPTION OF THE PREFERRED EMBODIMENTS

In a device for detecting a structure-borne sound signal, in particular for detecting a structure-borne sound signal triggered by an occurrence of damage on a component to be monitored, having at least one structure-borne sound sensor, at least one signal-conducting connection of the structure-borne sound sensor to an evaluation device and having a protective body, it is provided according to the invention that the structure-borne sound sensor comprises a structure-borne sound conducting connection to the protective body and that the protective body comprises a structure-borne sound conducting connection to the component to be monitored. The protective body of the device may be a protective housing. In said protective housing can be arranged the evaluation unit for the received structure-borne sound signals, for example. The structure-borne sound sensor, which can be configured as a piezoelectric film, for example, comprises a structure-borne sound-conducting connection to the protective body, in particular the piezoelectric film can be bonded to the protective body. In turn, the protective body comprises a sound-conducting connection to the component to be monitored, which is preferably configured as a planar component. A structure-borne sound signal due to an occurrence of damage or contact propagates on the component to be monitored and is transmitted to the protective body by means of the structure-borne sound-conducting connection. The structure-borne sound signal is detected by the structure-borne sound sensor on the protective body. In particular in planar components to be monitored, the structure-borne sound signals propagate as linearly dampened elastic oscillations. In this case, stretching and compression of the planar component may occur, propagating on the component in the form of a bending wave. The planar component can in particular be a glass pane. In the glass pane, it can be observed that the sheet is stretched on the top side to the same extent as it is compressed on the bottom side when a wave passes through. Stretching and compression of the component is transferred to the protective body and thus to the structure-borne sound sensor. Here, in particular an enforcement of the stretches and compressions by the protective body due to leverage effects may occur. This is reflected in an enhancement of the signal, whereas an increased signal intensity can be detected by the structure-borne sound sensor. A more sensible detection of structure-borne signals by the structure-borne sound sensor on the component to be monitored relative to a structure-borne sensor directly bonded to the component can therefore be present.

In a further development of the invention the protective space at least partially surrounds a cavity, at least one planar area of the protective space restricting the cavity is arranged approximately parallel to at least one surface of the component to be monitored and the structure-borne sound sensor is at least sectionally arranged on the restricting planar area of the protective body. The protective body may be a housing, for example, which can surround a cavity together with the component to be monitored, preferably a planar component. Here, a planar area of the protective body can be arranged approximately parallel to the surface of the component to be monitored. Preferably, the structure-borne sound sensor is arranged on the planar area parallel to the surface of the component to be monitored. A flexural oscillation propagating over the component to be monitored due to an occurrence of damage is thus directly transferred via the protective body to the structure-borne sensor. A particularly good enhancement of the stretching and compressions of the propagating flexural oscillation is enabled, as the lever forces of the framing of the protective body are not dampened by an inner filling of the protective body.

In another further development of the invention the structure-borne sound sensor is arranged on a planar region of the protective body restricting the cavity and the structure-borne sound sensor is arranged on a side facing the surface of the planar structure of the component to be monitored. Preferably, the protective body comprises a planar region which is arranged in parallel to the surface of the component to be monitored. For example, the protective body may comprise a framing running perpendicular to the planar region, wherein e.g. between the frame and the planar region a cavity can be formed. On the side of the planar region facing the cavity is arranged the structure-borne sound sensor. In particular, the structure-borne sound sensor can be configured as a piezoelectric film, which is attached to the planar region of the protective body by bonding, for example. By arranging the structure-borne sound sensor on the side of the planar region of the protective body facing the cavity, the structure-borne sound sensor is completely shielded against external impacts without resulting in a decrease of the mechanical enforcement of the structure-borne sound waves by the protective body.

In a constructive further development of the invention, the structure-borne sound sensor is spaced apart from the surface of the component to be monitored, which is arranged approximately parallel to the surface of the component to be monitored. By means of the spacing of the structure-borne sound sensor to the surface of the component to be monitored, a mechanical enforcement of the flexural oscillation or bending oscillation of the structure-borne sound signal due to leverage effect is to be expected.

In another constructive further development of the invention, the distance of the structure-borne sound sensor to the surface of the component to be monitored is a multitude of the thickness of the structure-borne sound sensor. In particular, the distance between the surface of the component to be monitored to the structure-borne sound sensor can be at least 1 mm, in particular at least 5 mm.

In an advantageous constructive further development of the invention, the device comprises a clamping device for fixing the device on the surface of the component to be monitored. The device may for example comprise one or more clamping arms, which are clamped to respective counterparts. The counterparts can for example directly be fixed to the surface to be monitored of the component. By means of this arrangement, a simple assembly as well as a simple disassembly of the device on the component to be monitored is possible. Thus, the device can be reused, in case the component to be monitored is damaged so severely that it needs to be replaced. A reuse of the device would not be possible if said device is fixedly bonded to the component to be monitored. Furthermore, the geometrical arrangement leads to an enhancement of the leverage effect by the compressions and stretching of the flexural oscillation of the structure-borne signal directly transmitted to the structure-borne sound sensor.

In a further development of the invention, the clamping device comprises at least two clamping arms. Said clamping arms can for example be at least sectionally flexibly configured protrusions extending from the protective body towards the component to be monitored. Counterparts may be arranged on the component to be monitored, to which the clamping arms can be clamped to.

In a preferred embodiment of the invention, the protective body is the protective body of an existing sensor system. Protective bodies for electronic switches, e.g. for electronic evaluation devices, are often used in vehicles for various purposes and on different positions. Here, it is possible to incorporate the device according to the invention in an already existing protective body. In this case, it can be considered an already existing evaluation unit, for example, so that additional electronics need not be installed. Consideration of already existing components leads to a considerable reduction of costs and time during assembly.

In one embodiment of the invention, the existing sensor system is a rain/light sensor. The integration of the device according to the invention into a rain/light sensor is particularly advantageous when monitoring a windshield of a vehicle. By means of the device according to the invention, the windshield can be checked for damages here. A rain/light sensor is usually arranged on a central position of the windshield, in order that structure-borne signals, which can e.g. be caused by a rock fall on the windshield can entirely be detected by the device integrated in the rain/light sensor.

Upon integration the structure-borne sound sensor may be bonded to the wall of the protective body of the rain/light sensor facing away from the windshield. In particular, the structure-borne sound sensor can be bonded to the side of the wall facing the windshield in order to make use of the protective function of the protective body for the structure-borne sound sensor.

In one embodiment of the invention, the structure-borne sound sensor is configured as a piezoelectric film. The use of piezoelectric films as structure-borne sound sensors is particularly advantageous since these can be produced in a cost-efficient way and are easy to install by means of bonding, for example.

In one embodiment of the invention, the component to be monitored is the windshield of a vehicle. By means of the device, it is possible to detect damages on a windshield by detection of structure-borne sound signals. By means of a pulse-like excitation, for example a rock fall, structure-borne sound oscillations are generated on a windshield. The structure-borne sound may propagate in the form of a linearly-dampened elastic oscillation of the windshield. Here, stretching and compression of the windshield occur, propagating on the component in the form of a flexural wave. The stretching and compression of the windshield are for example transferred through the protective body to the structure-borne sound sensor and can thus be detected by it. Also, an enhancement of the signal due to lever effects can be caused by the protective body, respectively by the clamping arms of the protective body, by means of which the protective body is for example installed on a windshield. The structure-borne sound signals detected by the structure-borne sound sensor can for example be evaluated in an evaluation device, and if the windshield is damaged, a signal can be output to the driver of the vehicle. Another aspect of the invention relates to a motor vehicle having a device according to the invention according to any one of the preceding claims. The use of structure-borne sound signal sensors for detecting occurrence of damage or contact is particularly advantageous in vehicles.

In the following, the invention is explained in more detail by means of a preferred exemplary embodiment illustrated in the drawings.

FIG. 1 illustrates a device according to the invention having a protective body 1, a structure-borne sound sensor 2 and a clamping device 3 on a component 4 to be monitored. The protective body 1 is clamped to the component 4 to be monitored by means of a clamping device 3. For this purpose, the clamping device 3 comprises a counterpart 5, by means of which a clamping arm of the clamping device 3 can be clamped. The protective body 1 is firmly pressed onto the surface to be monitored of the component 4 by means of the clamping device 3. The protective body 1 comprises a cavity 6. The structure-borne sound sensor 2 is configured as a piezoelectric film and arranged on the side of the wall facing the cavity 6, for example. By the leverage effect of the clamping device 3 a structure-borne sound signal is transmitted to the structure-borne sound sensor 2 in an enhanced manner.

FIG. 2 illustrates a perspective view of the device according to the invention. The protective body 1 is the protective body of a rain/light sensor. The protective body 1 comprises a clamping device 3 having two clamping arms 3a, 3b, which can for example be clamped to the component 4 to be monitored. In particular, the component to be monitored 4 can be a windshield of a motor vehicle.

The structure-borne sound sensor 2 is arranged on the side of the outer wall of the protective body 1 facing the cavity 6 in the form of a piezoelectric film. Together with the component to be monitored the protective body 1 forms the cavity 6. The structure-borne sound sensor 2 is arranged on the side of the outer wall of the protective body 1 facing away from the component 4 to be monitored. When using the device according to the invention, evaluation devices and data transmission devices of the rain/light sensor may be considered.

All features mentioned in the preceding description and in the claims can be combined in any selection with the features of the independent claim. The disclosure of the invention is thus not limited to the feature combinations claimed or described; in fact all appropriate combinations of features within the scope of the invention shall be considered to be disclosed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A device for detecting a structure-borne sound signal, having at least one structure-borne sound sensor, at least one signal-conducting connection of the at least one structure-borne sound sensor to an evaluation device and having a protective body,
   wherein
   the at least one structure-borne sound sensor comprises a structure-borne sound conducting connection to the protective body,
   the protective body comprises a structure-borne sound conducting connection to the component to be monitored, and
   the protective body at least sectionally surrounds a cavity,
   at least one planar region of the protective body restricting the cavity is arranged approximately parallel to at least one surface of the component to be monitored, and
   the at least one structure-borne sound sensor is at least sectionally arranged on the at least one restricting planar region of the protective body.

2. The device according to claim 1, wherein the at least one structure-borne sound sensor is arranged in the at least one planar region of the protective body restricting the cavity and the at least one structure-borne sound sensor is arranged on the side of the at least one planar region of the protective body facing the component to be monitored.

3. The device according to claim 1, wherein the at least one structure-borne sound sensor is spaced apart from the surface of the component to be monitored.

4. The device according to claim 3, wherein the distance of the at least one structure-borne sound sensor to the surface of the component to be monitored is many times greater than the thickness of the at least one structure-borne sound sensor.

5. The device according to claim 1, wherein the device comprises a clamping device for fastening the device to the surface of the component to be monitored.

6. The device according to claim 5, wherein the clamping device comprises at least two clamping arms.

7. The device according to claim 1, wherein the protective body is the protective body of an existing sensor system.

8. The device according to claim 7, wherein the existing sensor system is a rain/light sensor.

9. The device according to claim 1, wherein the at least one structure-borne sound sensor is configured as a piezoelectric film.

10. The device according to claim 1, wherein the component to be monitored is the windshield of a vehicle.

11. A vehicle, having a device according to claim 1.

12. The vehicle according to claim 11, wherein the vehicle is a motor vehicle.

13. The device according to claim 1, wherein the structure-borne sound signal is triggered by an occurrence of damage on a component to be monitored.

* * * * *